US009579510B2

(12) United States Patent
Meskens (10) Patent No.: US 9,579,510 B2
(45) Date of Patent: Feb. 28, 2017

(54) IMPLANTABLE REMOTE CONTROL (75) Inventor: Werner Meskens, Mechelen (BE)

(73) Assignee: Cochlear Limited, Macquarie University (AU)

( * ) Notice: Subject to any disclaimer, the term of this patent is extended or adjusted under 35 U.S.C. 154(b) by 337 days.

(21) Appl. No.: 13/186,178

(22) Filed: Jul. 19, 2011

(65) Prior Publication Data

US 2013/0023954 A1 Jan. 24, 2013

(51) Int. Cl.
*A61N 1/00* (2006.01)
*A61N 1/372* (2006.01)
*G06F 3/01* (2006.01)
*G06F 19/00* (2011.01)
*A61N 1/36* (2006.01)

(52) U.S. Cl.
CPC ..... *A61N 1/37252* (2013.01); *A61N 1/37217* (2013.01); *G06F 3/017* (2013.01); *G06F 19/3406* (2013.01); *A61N 1/36032* (2013.01); *A61N 1/37247* (2013.01)

(58) Field of Classification Search
CPC ............ A61N 1/36032; A61N 1/37247; H04R 25/558; H04R 2225/51; Y10S 128/903; G06F 3/014
USPC ............. 607/2, 7, 18, 19, 56, 57, 59, 60, 62
See application file for complete search history.

(56) References Cited

U.S. PATENT DOCUMENTS

| | | | |
|---|---|---|---|
| 5,553,152 A * | 9/1996 | Newton | 381/328 |
| 5,626,629 A * | 5/1997 | Faltys et al. | 607/57 |
| 6,161,046 A * | 12/2000 | Maniglia et al. | 607/57 |
| 6,564,807 B1 | 5/2003 | Schulman et al. | |
| 7,577,459 B2 | 8/2009 | Tuomela et al. | |
| 2005/0209657 A1 * | 9/2005 | Chung et al. | 607/57 |
| 2007/0047749 A1 | 3/2007 | Kasztelan et al. | |
| 2007/0055949 A1 * | 3/2007 | Thomas | 715/863 |
| 2007/0239992 A1 | 10/2007 | White et al. | |
| 2007/0265508 A1 * | 11/2007 | Sheikhzadeh-Nadjar et al. | 600/300 |
| 2008/0025537 A1 | 1/2008 | Ritter et al. | |
| 2009/0079576 A1 | 3/2009 | Yankelevitz et al. | |

(Continued)

FOREIGN PATENT DOCUMENTS

| | | |
|---|---|---|
| EP | 1160651 A1 | 12/2001 |
| EP | 2302885 A1 | 3/2011 |

(Continued)

OTHER PUBLICATIONS

Microchip implant (human)—Wikipedia, the free encyclopedia; http://en.wikipedia.org/wiki/Microchip_implant_(human); printed from the worldwide web on Jul. 18, 2011.

(Continued)

*Primary Examiner* — William Levicky
*Assistant Examiner* — Lindsey G Hankins
(74) *Attorney, Agent, or Firm* — McDonnell Boehnen Hulbert & Berghoff LLP (57) ABSTRACT

The present application discloses systems, methods, and articles of manufacture for controlling one or more functions of a device utilizing one or more tags. In one example, a method for controlling one or more functions of a medical device includes scanning a data interface of the medical device for signals induced wirelessly by one or more gestures made with one or more tags associated with a recipient of the medical device and controlling one or more functions of the medical device based on the wirelessly induced signals.

37 Claims, 3 Drawing Sheets

(56) References Cited

U.S. PATENT DOCUMENTS

2009/0163980 A1    6/2009  Stevenson
2009/0208043 A1*   8/2009  Woods et al. .................. 381/315
2011/0044483 A1*   2/2011  Edgar ........................... 381/314

FOREIGN PATENT DOCUMENTS

WO    WO2005121939 A2    12/2005
WO    WO2008121492 A1    10/2008
WO    WO2010083389 A1     7/2010

OTHER PUBLICATIONS

U.S. employees VeriChipped; http://www.spchips.com/prss-releases/us-employees-verichipped.html: Feb. 9, 2006.
International Search Report and Written Opinion of International Application No. PCT/IB2012/053698 dated Feb. 28, 2013 (mailed Mar. 4, 2013).

* cited by examiner

IMPLANTABLE REMOTE CONTROL

BACKGROUND

Various types of hearing prostheses may provide persons with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound and a vibration mechanism to apply vibrations corresponding to the detected sound to a person's bone, thereby causing vibrations in the person's inner ear and bypassing the person's auditory canal and middle ear. Vibration-based hearing devices may include bone anchored devices, direct acoustic cochlear stimulation devices, or other vibration-based devices. A bone anchored device typically utilizes a surgically-implanted mechanism to transmit vibrations corresponding to sound via the skull. A direct acoustic cochlear stimulation device also typically utilizes a surgically-implanted mechanism to transmit vibrations corresponding to sound, but bypasses the skull and more directly stimulates the inner ear. Other non-surgical vibration-based hearing devices may use similar vibration mechanisms to transmit sound via direct vibration of teeth or other cranial or facial bones.

Persons with certain forms of sensorineural hearing loss may benefit from prostheses, such as cochlear implants and/or auditory brainstem implants. For example, cochlear implants may provide a person having sensorineural hearing loss with the ability to perceive sound by stimulating the person's auditory nerve via an array of electrodes implanted in the person's cochlea. A component of the cochlear implant detects sound waves, which are converted into a series of electrical stimulation signals delivered to the implant recipient's cochlea via the array of electrodes. Auditory brainstem implants may use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem may enable persons with sensorineural hearing loss to perceive sound.

Such prostheses typically include a user interface to control various functions thereof. For example, the user interface may include physical buttons, switches, dials, and the like that are disposed on a prosthesis and used to turn the prosthesis on and off, to adjust the volume, change settings or operating modes, adjust other audio processing parameters, such as gain, sensitivity, frequency filtering, etc. In another example, the user interface may include a separate remote control that communicates with the prosthesis in any known wired or wireless manner, such as through a radio frequency, infrared light, laser light, and/or visible light signal.

SUMMARY

The present application discloses systems, methods, and articles of manufacture for allowing a user to control various functions of a device, such as a hearing prosthesis. In some embodiments, one or more tags are used that communicate wirelessly with the device. The tag(s) may be attached to the user's hand, such as on or under the skin of the user's fingers. In another example, the tag(s) may be coupled to fingertips of a glove or a ring-type structure.

Some embodiments are directed to a method for controlling one or more functions of a medical device and include scanning a data interface of the medical device for signals induced wirelessly by one or more gestures made with one or more tags associated with a recipient of the medical device and controlling one or more functions of the medical device based on the wirelessly induced signals. In some embodiments, the medical device may be fully or partially implanted in a recipient. In other embodiments, the medical device may be an external device worn by the recipient rather than implanted in the recipient.

Other embodiments may include a medical device that has a data interface configured to receive wireless signals induced by a one or more of a plurality of tags associated with a recipient of the medical device and a processor configured to interpret the induced signals to control a plurality of functions of the medical device.

Yet other embodiments may be directed to a method of operating a device that includes scanning the device for signals induced wirelessly by one or more tags implanted in a user of the device, processing the wirelessly induced signals to identify one or more gestures made with the one or more tags, and performing one of a plurality of functions of the device in response to the one or more gestures.

Further embodiments may be directed to a device that includes means for receiving signals from user coupled means for wirelessly inducing such signals and means for interpreting the induced signals as one or more gestures made by the user coupled means to control one or more functions of the device.

Still other embodiments may include an article of manufacture with computer readable media having instructions encoded thereon for interpreting signals induced wirelessly at a data interface of a device by one or more of a plurality of tags and for controlling a plurality of functions of the device in accordance with the wirelessly induced signals.

DETAILED DESCRIPTION

The following detailed description describes various features, functions, and attributes of the disclosed systems, methods, and articles of manufacture with reference to the accompanying figures. In the figures, similar symbols typically identify similar components, unless context dictates otherwise. The illustrative embodiments described herein are not meant to be limiting. Certain aspects of the disclosed systems, methods, and articles of manufacture can be arranged and combined in a wide variety of different configurations, all of which are contemplated herein.

For illustration purposes, some features and functions are described with respect to cochlear implants. However, many features and functions may be equally applicable to other types of hearing prostheses and to other types of devices, including other types of medical and non-medical devices.

Figure 1:
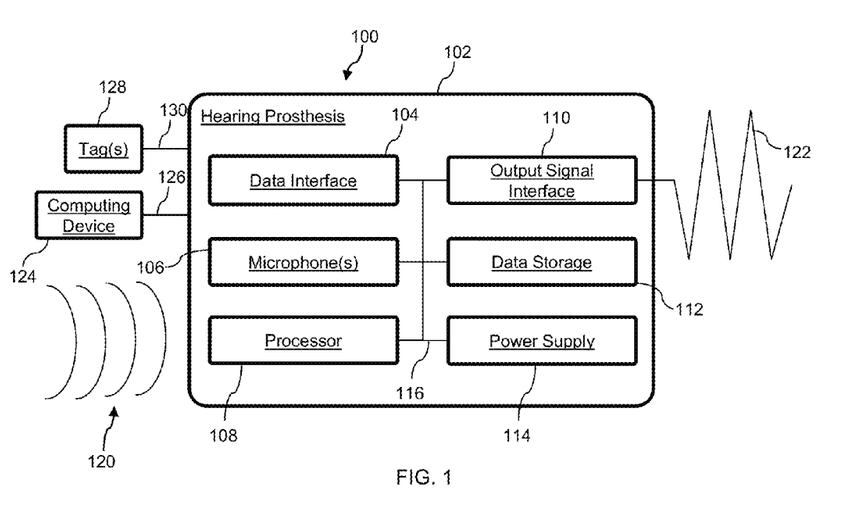
FIG. 1 illustrates a block diagram of a hearing prosthesis system according to an embodiment of the present disclosure.

FIG. 1 shows one example system 100 that includes a hearing prosthesis 102 configured according to some embodiments of the disclosed systems, methods, and articles of manufacture. The hearing prosthesis 102 may be a cochlear implant, an acoustic hearing aid, a bone anchored device, a direct acoustic stimulation device, an auditory brain stem implant, or any other type of hearing prosthesis configured to assist a prosthesis recipient in perceiving sound.

The hearing prosthesis 102 illustrated in FIG. 1 includes a data interface 104, one or more microphones 106, one or more microcontrollers or processors 108, an output signal interface 110, data storage 112, and a power supply 114 all of which may be connected directly or indirectly via a system bus or other known circuitry 116. The one or more microphones 106 may include combinations of one or more omnidirectional and directional microphones so that the hearing prosthesis 102 can be configured to process background sounds and/or to focus on sounds from a specific direction, such as generally in front of the prosthesis recipient. Further, the power supply 114 supplies power to various components of the hearing prosthesis 102 and may be any suitable power supply, such as a non-rechargeable or rechargeable battery. In one example, the power supply 114 is a battery that can be recharged wirelessly, such as through inductive charging. Such a wirelessly rechargeable battery would facilitate complete subcutaneous implantation of the hearing prosthesis 102 to provide a fully-implantable prosthesis. A fully implanted medical device, such as a fully implanted hearing prosthesis, has the added benefit of enabling the recipient to engage in activities that expose the recipient to water or high atmospheric moisture, such as swimming, showering, saunaing, etc., without the need to remove, disable or protect, such as with a water/moisture proof covering or shield, the medical device. A fully implanted medical device also spares the recipient of stigma, imagined or otherwise, associated with use of the medical device.

The data storage 112 may include any suitable volatile and/or non-volatile storage components. Further, the data storage 112 may include computer-readable program instructions and perhaps additional data. In some embodiments, the data storage 112 may store data and instructions used to perform at least part of the herein-described methods and algorithms and/or at least part of the functionality of the systems described herein.

Various modifications can be made to the hearing prosthesis 102 illustrated in FIG. 1 without departing from the spirit of the present disclosure, for example, the prosthesis may include additional or fewer components arranged in any suitable manner. Further, depending on the type and design of the hearing prosthesis 102, the illustrated components may be enclosed within a single operational unit or distributed across multiple operational units (e.g., two or more internal units or an external unit and an internal unit).

Generally, in use, the microphone(s) 106 are configured to receive external acoustic signals 120 and the processor 108 is configured to analyze and encode the acoustic signals into output signals 122 for application to the implant recipient via the output signal interface 110.

More particularly, in embodiments where the hearing prosthesis 102 is a cochlear implant, the microphone(s) 106 may be configured to receive external acoustic signals 120, and the processor 108 may be configured to analyze and encode the acoustic signals into electrical stimulation output signals 122 for application to an implant recipient's cochlea via the output signal interface 110, which may include an array of electrodes, for example. In one example, the hearing prosthesis 102 is a cochlear implant similar or identical to a Cochlear™ Nucleus® hearing prosthesis.

In embodiments where the hearing prosthesis 102 is an acoustic hearing aid, the microphone(s) 106 may be configured to receive acoustic signals 120, and the processor 108 may be configured to analyze and encode the acoustic signals into acoustic output signals 122 for applying to a recipient's ear via the output signal interface 110 comprising a speaker, for example.

For embodiments where the hearing prosthesis 102 is a bone anchored device, the microphone(s) 106 may be configured to receive acoustic signals 120, and the processor 108 may be configured to analyze and encode the acoustic signals into mechanical vibration output signals 122 for applying to the bone anchored device recipient's skull via the output signal interface 110 that may include a mechanism to transmit sound via direct bone vibrations. In one example, the hearing prosthesis 102 is a bone anchored device similar or identical to a Cochlear™ Baha® bone anchored device.

Similarly, for embodiments where the hearing prosthesis 102 is a direct acoustic cochlear stimulation (DACS) device, the microphone(s) 106 may be configured to analyze and encode the acoustic signals 120 into mechanical vibration output signals 122 for applying to the DACS recipient's inner ear via the output signal interface 110 that may include a mechanism to transmit sound via direct vibration. In addition, for embodiments where the hearing prosthesis 102 is an auditory brain stem implant, the microphone(s) 106 may be configured to analyze and encode the acoustic signals 120 into electrical stimulation output signals 122 for applying to the auditory brain stem implant recipient's auditory nerve via the output signal interface 110 that may include one or more electrodes.

Referring now to the data interface 104, the interface may be utilized to load a recipient's program or "MAP" into the prosthesis 102 and stored in the data storage 112. A recipient's program or MAP allows the hearing prosthesis to be configured for or fitted to a recipient and generally includes configuration settings and other data that defines how the processor 108 of the prosthesis 102 analyzes and converts acoustic signals 120 received by the microphone(s) 106 to output signals 122 transmitted to the prosthesis recipient via the output signal interface 110. Typically, a computing device 124 can be used to execute fitting software for a particular hearing prosthesis 102 and load the recipient's program to the data interface 102 through a communication connection 126. The communication connection 126 may be any suitable wired connection, such as an Ethernet cable, a Universal Serial Bus connection, a twisted pair wire, a coaxial cable, a fiber-optic link, or a similar physical connection, or any suitable wireless connection, such as Bluetooth, Wi-Fi, WiMAX, and the like.

The data interface 104 may also be utilized by the recipient or a third party, such as a guardian of a minor recipient or a health care professional, to control various functions of the hearing prosthesis 102. The functions may include, for example, turning the prosthesis 102 on and off, adjusting the volume, switching between one or more operating modes, adjusting other audio processing parameters, such as gain, sensitivity, frequency filtering, etc. Operating modes may include, by way of non-limiting examples, a telephone mode for use with a telephone handset or mobile phone, a direct audio mode that connects the prosthesis directly to an audio source, such as a music player, television, public address system, etc., an omnidirectional microphone mode that processes all background sounds received by the microphone(s) 106, and a directional microphone mode that amplifies or focuses on sounds coming from a specific direction, such as sounds coming from in front of the recipient.

In the embodiment of FIG. 1, one or more tags 128 may be used by the recipient or third party to communicate with the hearing prosthesis 102 via the data interface 104 and a communication connection 130 to control the various functions of the hearing prosthesis 102. In one example, the tag(s) 128 are self-contained devices that are able to communicate wirelessly with the data interface 104 without a power source directly coupled thereto. Although in some examples, a power source may be directly coupled to the tag(s) 128. In one example, the data interface 104 includes a suitable transmitter/receiver for transmitting electrical, magnetic, and/or electromagnetic signals and receiving a return signal induced by the tag(s) 128. Such return signals may then be processed and interpreted by a processor, such as the processor 108, to uniquely or generically identify each of the one or more tags 128 and to control one or more functions of the hearing prosthesis 102.

The hearing prosthesis 102 may be programmed by the computing device 124 via the communication connection 126 to the data interface 104 to identify one or more tags 128, to identify gestures made by the tag(s), as will be described in more detail hereinafter, and to control one or more functions of the hearing prosthesis 102. Such programming may be performed during a fitting session of the hearing prosthesis 102 to the user or at any other appropriate time to associate the tag(s) 128 with user and the prosthesis 102.

Figure 2:
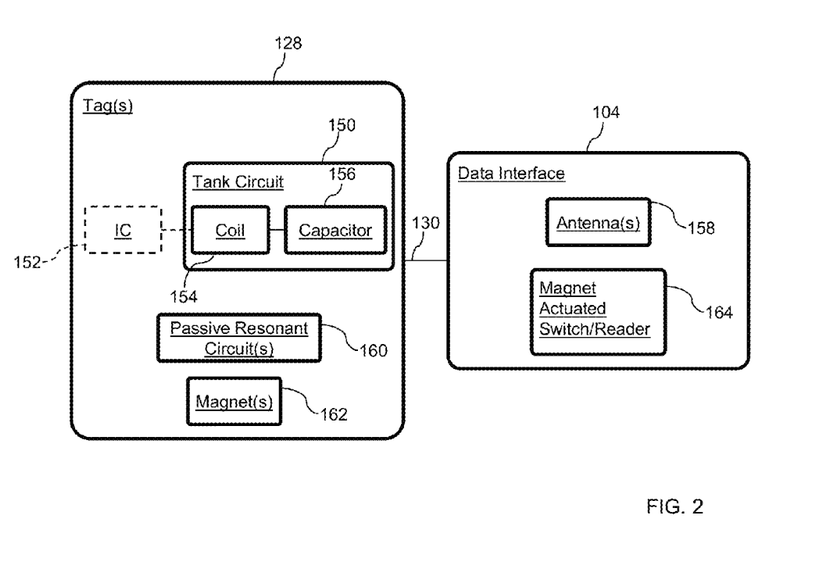
FIG. 2 illustrates a block diagram of the tag(s) and the data interface of FIG. 1 according to another embodiment of the present disclosure.

Referring now to FIG. 2, the tag(s) 128 may include a resonant tank circuit 150, which has, for example, an integrated circuit 152 coupled to an inductor or coil 154 and a capacitor 156, similar to known tank circuits used as radio frequency identification (RFID) tags. The tag(s) 128 may be passive RFID tags that can be read by the data interface 104, which may include one or more suitable antennas 158, such as a loop antenna, an open dipole antenna, and the like. In one example, the antenna 158 is a loop antenna with a small number of turns, for example, two turns with a relatively large diameter, which increases detectability of the tag(s) 128 and reduces the power consumption needed to transmit signals therefrom. In another example, the antenna 158 includes multiple antennas arranged in an array, which may facilitate the interpretation of gestures made by the tag(s) 128, as described in more detail herein.

In another example, the tag(s) 128 may include one or more passive resonant circuits 160. The passive resonant circuit(s) 160 may be formed from an LC circuit, such as the tank circuit 150 including the inductor 154 and the capacitor 156 without the optional integrated circuit 152. Other passive resonant circuit(s) 160 may include ceramic and/or piezoelectric material resonators, for example, whereby the circuit(s) 160 may be actuated or energized and a resonant frequency of the resonator detected by the antenna(s) 158, for example.

In yet another example, the tag(s) 128 may include one or more magnets 162 and the data interface 104 may include a magnetosensitive element or reader 164 for detecting the presence of the magnet(s). Such magnetosensitive element or reader 162 may include, for example, a hall sensor, a reed switch, and/or a giant magneto-resistive sensor for detecting a magnetic field generated by the magnet(s) 162. In the present example, the processor 108 is configured to interpret the presence of the magnetic field generated by the magnets 162 to control one or more functions of the prosthesis 102.

In accordance with another example of the present disclosure, the tag(s) 128 are configured to be disposed on a user, such as by being implanted subcutaneously under the skin of the recipient or third party or otherwise attached over the skin of the recipient or third party. For example, in some embodiments, the user may correspond to a recipient's parent or caregiver. A benefit of the tag(s) 128 being implanted subcutaneously under the skin is that the user can engage in activities that expose the user to water or high atmospheric moisture, such as swimming, showering, saunaing, etc., without the need to remove, disable or protect, such as with a water/moisture proof covering or shield, the tag(s) 128. Yet another benefit of the tag(s) 128 being implantable subcutaneously under the skin is that the user cannot lose the tag(s) and his or her ability to control the prosthesis 102.

Figure 3:
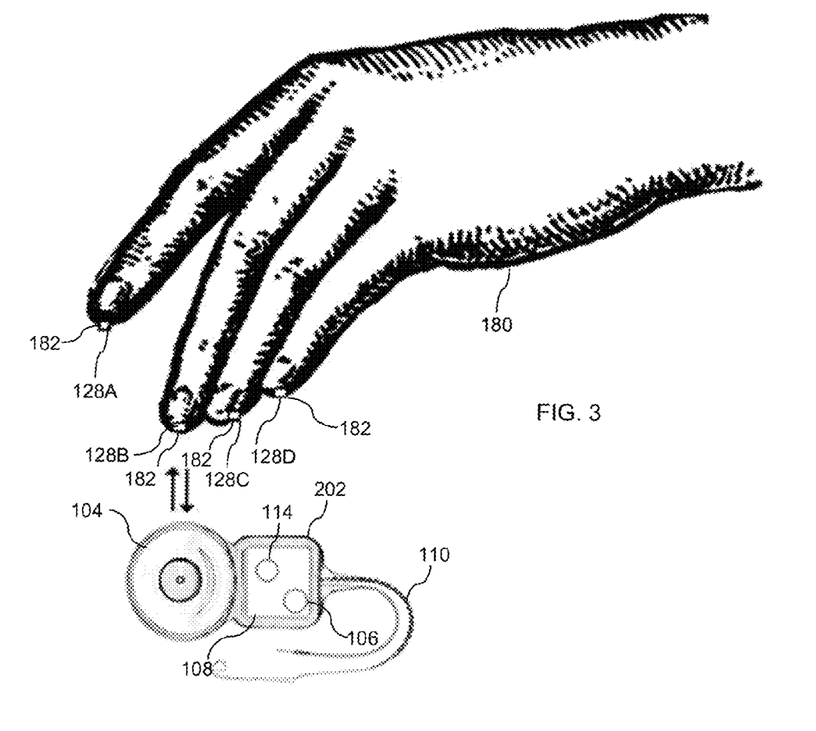
FIG. 3 is a diagrammatic illustration of the hearing prosthesis system of FIG. 1 in accordance with an embodiment.

Alternatively, the tag(s) 128 may be disposed on a structure worn, associated with, or attached to a user, such as by being disposed on fingertips of a glove, on one or more rings, on one or more bracelets, incorporated into a watch, coupled to a cellular phone, and the like. FIG. 3 illustrates an example, where a plurality of tags 128A, 128B, 128C, and 128D are disposed on or subcutaneously in finger tips of the user's hand 180. The tags 128A-128D may be protected by or disposed in a biocompatible layer or housing 182 that allows for the transmission of electrical and/or magnetic fields therethrough. One or more of the tags 128A-128D may be identified uniquely by a hearing prosthesis 202, for example by a having distinct RFID tags or a magnets with unique magnetic fields. Such unique magnetic fields may be generated by different orientations of the north and south poles of the magnets with respect to fingers of the user and/or by magnets having magnetic fields of different magnitude. The hearing prosthesis 202 of FIG. 3 illustrates some but not all of the components of FIG. 1, it being understood that the prosthesis 202 may include additional components that are not visible in FIG. 3.

Figure 4A:
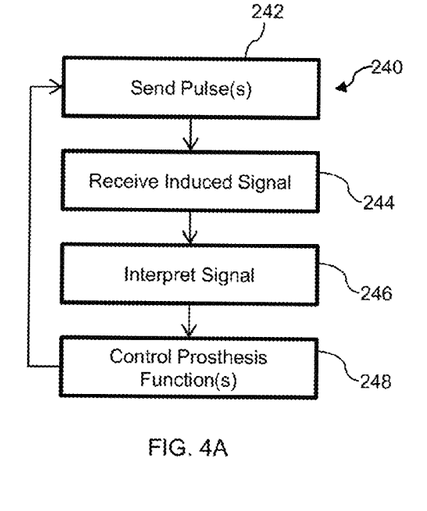
FIGS. 4A and 4B are flowcharts showing examples of methods for controlling various functions of the hearing prosthesis of FIG. 1.

Referring now more particularly to FIG. 4A and with further reference to FIGS. 1-3, one example method 240 is illustrated for controlling various functions of a hearing prosthesis utilizing one or more RFID or similar tags 128 and a data interface 104 that includes one or more antenna(s) 158, for example. At a block 242, the antenna(s) 158 are energized to generate a pulse or a series of pulses, such as RF signal pulses. In one example, a series of pulses having a duration of about 1 ms to about 10 ms are generated about every 100 ms to about every 500 ms. Such periodic pulses help to conserve power consumption by the hearing prosthesis 102. Thereafter, control passes to a block 244 to control the processor 108 to scan the data interface 104 for any signals induced by the presence of one or more tags 128. In one example, the pulses generated by the antenna(s) 158 excite the coil 154 of a nearby tag 128 and charge the capacitor 156, which in turn energizes and powers the IC 152. The IC 152 then transmits identifying information via the coil 154 to the data interface 104. In another example, the block 244 can be performed before, during, and/or after the generation of the pulses at the block 242. Next, control passes to a block 246 and the processor 108 interprets such identifying information to control one or more functions of the prosthesis 102 at a block 248. Thereafter, the control may loop back to the block 242 to repeat the method 240.

In one non-limiting example of the block 248, if the unique tag 128A is identified by the processor 108, then the processor 108 may turn off the hearing prosthesis 202. If the unique tag 128B is identified by the processor 108, then the processor 108 may turn on the hearing prosthesis 202. If the unique tag 128C is identified by the processor 108, then the processor 108 may turn the volume up on the hearing prosthesis 202, and if the unique tag 128D is identified by the processor 108, then the processor 108 may turn the volume down.

Figure 4B:
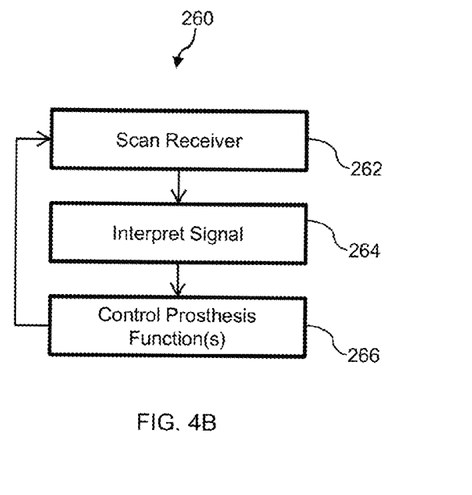

Referring now more particularly to FIG. 4B and with further reference to FIGS. 1-3, another example method 260 is illustrated for controlling various functions of a hearing prosthesis utilizing magnetic or similar tags 128 and one or more magnetosensitive element 164. At a block 262, the processor 108 is controlled to scan the data interface 104 for any signals induced by the presence of one or more tags 128. In one example, a tag 128 brought into proximity of the magnetosensitive element(s) 164 induces a signal that is interpreted by the processor at a block 264. Control then passes to a block 266 to control one or more functions of the prosthesis 102, 202 in accordance with the induced signal. Thereafter, control may loop back to the block 262 to repeat the method 260.

Figure 5:
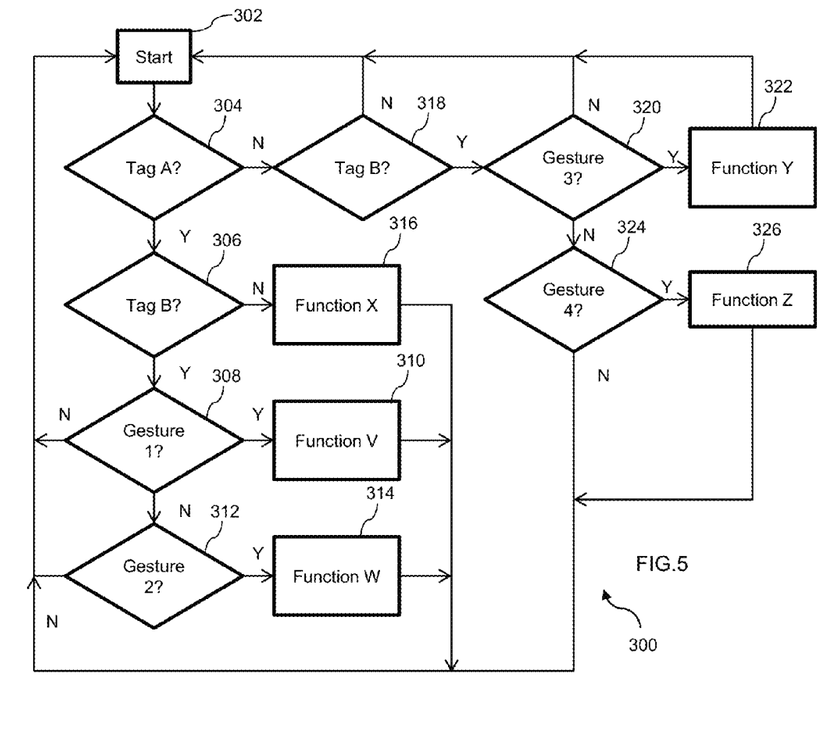
FIG. 5 is a flowchart showing an example of an algorithm for controlling various functions of the hearing prosthesis of FIG. 1.

Referring now to FIG. 5, an example algorithm 300 is illustrated for interpreting signals induced by the tag(s) 128 to control functions of hearing prostheses, such as the hearing prostheses 102, 202 disclosed herein. More particularly, the algorithm 300 is adapted to interpret gestures made by one or more tags 128 brought into proximity with the data interface 104. To facilitate the interpretation of gestures, a processor, such as the processor 108 described above, is configured to interpret signals induced at the data interface 104 by the tag(s) 128 to determine characteristics of movement of such tags, such as a direction of movement, speed, acceleration, etc. To further facilitate the interpretation of gestures, the data interface 104 may include an array of transmitters/receivers, such as an array of antennas 158 and/or an array of magnetosensitive elements or readers 164.

The algorithm 300 begins at a start block 302 and passes to a decision block 304. The decision block 304 determines if a first tag A, such as the tag 128A, has induced a signal at the data interface 104. If so, control passes to a block 306, which determines if a second tag B, such as the tag 128B, has also induced a signal at the data interface 104. If so, control passes to a decision block 308, which determines if a first gesture has been made with the tags 128A, 128B.

Generally, a gesture may be characterized by the detection of two or more tags 128 brought into proximity of the hearing prosthesis 102, 202 and being generally held stationary for a predetermined time period, such as for between about 0.5 to 1.0 seconds. Alternatively or in conjunction, a gesture may be characterized by the detection of a predetermined movement of one or more tags 128. The predetermined movement may be a relatively simple linear movement or a complex multi-part series of movements, including non-linear movement and speed and/or direction changes, for example. Consequently, a multitude of different gestures can be used to control any desired function of a hearing prosthesis 102, 202 or any other suitable device. The complexity of such gestures may depend, in part, on the dexterity or abilities of the user. For example, for an individual with limited finger dexterity the gestures may be fairly simple, such as bringing one or more tags into proximity of the device for a predetermined time period. For an individual with good finger dexterity the gestures may be more complex and include, for example, non-linear movement, direction changes, tapping motions, etc.

Referring again to the decision block 308, in one example, the tag 128A is disposed proximate a tip of a recipient's index finger and the tag 128B is disposed proximate a tip of a recipient's middle finger. In the present example, the first gesture is characterized by holding both tags 128A, 128B together, bringing them proximate to the data interface 104, which may be disposed on a side of the recipient's head, and moving both tags forward generally toward the recipient's eyes. If the decision block 308 determines that the first gesture is being made, control passes to a block 310 and the prosthesis 102, 202 is controlled to implement a function V. In the present example, the function V is to implement a directional microphone mode that amplifies or focuses on sounds coming from in front of the recipient. After the block 310, control passes back to the start 302.

If the first gesture is not detected at the block 308, control passes to a decision block 312 to determine if a second gesture has been made with the tags 128A, 128B. In the present example, the second gesture is characterized by holding both tags 128A, 128B together, bringing them proximate to the data interface 104, which may be disposed on a side of the recipient's head, and moving the tags away from each other. If the decision block 312 determines that the second gesture is being made, control passes to a block 314 and the prosthesis 102, 202 is controlled to implement a function W. In the present example, the function W is to implement an omnidirectional microphone mode that processes all sounds received by the microphone(s) 106, including background sounds. Thereafter, control passes back to the start 302.

Referring back to the decision block 306, if the second tag B is not detected, then control passes to a block 316 and the prosthesis 102, 202 is controlled to implement a function X. In the present example, the function X corresponds to only tag A being brought into proximity with the data interface 104, to turn the prosthesis 102, 202 on and off. Thereafter, control passes back to the start 302.

At the decision block 304, if the tag A has not been detected, control passes to a block 318 to determine if the tag B has been detected. If not, control passes back to the start 302. If the block 318 detects the tag B, then control passes to a decision block 320 to determine if a third gesture is being made. In the present example, the third gesture is characterized by bringing only the tag B into proximity with the data interface 104 and moving the tag B upwardly. If the decision block 320 determines that the third gesture is being made, control passes to a block 322 and the prosthesis 102, 202 is controlled to implement a function Y. In the present example, the function Y is to turn up the volume on the prosthesis 102, 202. Thereafter, control passes back to the start 302.

At the decision block 320, if the third gesture is not being made, control passes to a decision block 324 to determine if a fourth gesture is being made. In the present example, the fourth gesture is characterized by bringing only the tag B into proximity with the data interface 104 and moving the tag B downwardly. If the decision block 324 determines that the fourth gesture is being made, control passes to a block 326 and the prosthesis 102, 202 is controlled to implement a function Z. In the present example, the function Z is to turn down the volume on the prosthesis 102, 202. Thereafter, control passes back to the start 302. Control also passes back to the start 302 if the decision block 324 determines that the fourth gesture is not being made.

In another example, the blocks 320-326 may also take into account a length of time that the tag B is held after being moved upwardly or downwardly. In the present example, the length of time that the tag B is held may correspond to a level of the volume increase or decrease and/or may correspond to a speed of the volume increase or decrease.

Various modifications may be made to the illustrative example of FIG. 5 without departing from the spirit of the present disclosure. For example, the algorithm 300 may detect the presence of additional or fewer tags and/or gestures. The algorithm 300 may also take into account different characteristics of the gestures to further control different functions of the hearing prosthesis 102, 202. For example, the speed, direction, acceleration, and/or distance traveled of the gestures may be taken into account to control the different functions. Utilizing such characteristics, one or more tags may be used as input devices to control complex functions of the devices and/or to input data to the device. Further, additional, fewer, and/or different functions may be performed in any suitable order in response to the various determinations.

In some embodiments, the disclosed features and functions of the systems, methods, and algorithms shown and described herein may be implemented as computer program instructions encoded on a computer readable media in a machine-readable format.

Figure 6:
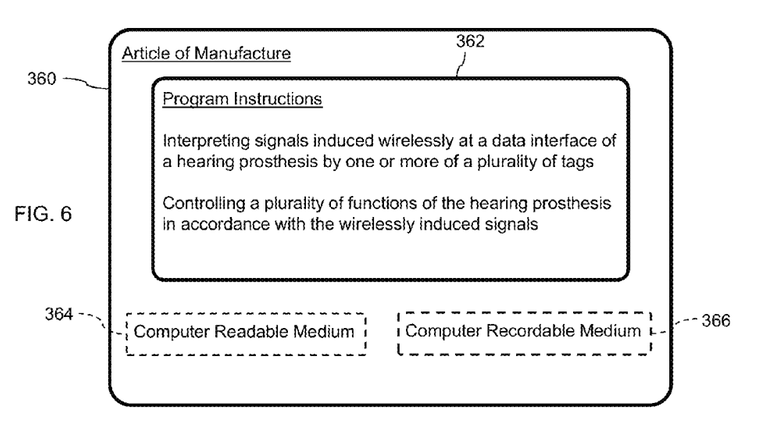
FIG. 6 is a block diagram of an article of manufacture including computer readable media with instructions for causing one or more processors or controllers to execute a method for controlling various functions of the hearing prosthesis of FIG. 1.

FIG. 6 shows an example of an article of manufacture 360 including computer readable media with instructions 362 for controlling one or more functions of a hearing prosthesis 102 in accordance with control signals induced wirelessly by one or more tags 128 disposed on a user. FIG. 6 shows a schematic illustrating a conceptual partial view of an example article of manufacture 360 that may include computer program instructions 362 for executing a computer process on a computing device, arranged according to at least some embodiments described herein.

In some examples, the article of manufacture 360 may include a computer-readable medium 364, such as, but not limited to, a hard disk drive, a Compact Disc (CD), a Digital Video Disk (DVD), a digital tape, flash memory, etc. In some implementations, the article of manufacture 360 may include a computer recordable medium 366, such as, but not limited to, a hard disk drive, a Compact Disc (CD), a Digital Video Disk (DVD), a digital tape, flash memory, etc.

The one or more programming instructions 362 may include, for example, computer executable and/or logic implemented instructions. In some embodiments, a computing device such as the computing device 124 shown and described in FIG. 1, alone or in combination with one or more additional processors or computing devices, may be configured to perform certain operations, functions, or actions to implement the features and functionality of the disclosed systems and methods based at least in part on the programming instructions 362. In still other embodiments, the processor 108 of the prosthesis 102, alone or in combination with one or more other processors associated with the prosthesis, may be configured to perform various operations, functions, or actions to implement the features and functionality of the disclosed systems and methods based at least in part on the programming instructions 362.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Further, while various aspects and embodiments of the present disclosure have been described with particular reference to hearing prostheses, the present disclosure contemplates application of the concepts disclosed herein to other types of devices. Such devices may include, for example, other medical devices that may or may not be implanted in a recipient. Some non-limiting examples of such medical devices include pacemakers, cardioverter-defibrillators, drug delivery systems, etc. In addition, the present disclosure may find application in the manipulation and control of non-medical devices, such as audio/video equipment, smartphones, touch pads, household fixtures, and the like. Depending on the device, different functions and/or modes can be controlled utilizing one or more tags.

Further, as discussed above, a device, for example, the hearing prosthesis 102 of FIG. 1, may be configured to detect the presence of one or more tags 128 brought into proximity with the data interface 104. The term proximity is a general term and an actual distance between the tag(s) 128 and the data interface 104 needed to detect the tags may depend on the configuration of the tags and the data interface and the specific device. In the example of the hearing prosthesis 102, the device may be configured such that the data interface 104 will detect the tag(s) 128 when the tag(s) are within about 4 cm or less of the data interface. However, in other examples with other devices, tags may be detected at shorter or farther distances.

What is claimed is:

1. A method, comprising:
    scanning a data interface of a medical device for signals induced wirelessly by one or more gestures made with one or more tags of a plurality of tags, wherein each gesture consists only of each of the one or more tags being within about 4 centimeters or less of the data interface;
    identifying individual tags of the one or more tags of the plurality of tags based on the wirelessly induced signals; and
    controlling a plurality of functions of the medical device based on the wirelessly induced signals and the identified individual tags,
    wherein controlling the plurality of functions of the medical device based on the wirelessly induced signals and the identified individual tags includes selecting one of a plurality of operating modes for the medical device and causing the medical device to operate in the selected operating mode.

2. The method of claim 1, further comprising generating signal pulses, wherein the signal pulses interact with the one or more tags to generate the wirelessly induced signals, and interpreting the wirelessly induced signals to identify uniquely each tag of the one or more tags.

3. The method of claim 2, wherein a first gesture made with a first tag corresponds to controlling a first function of turning the medical device on, a second gestures made with a second tag corresponds to controlling a second function of turning the medical device off, a third gesture made with a third tag corresponds to controlling a third function of turning a medical device volume up, and a fourth gesture made with a fourth tag corresponds to controlling a fourth function of turning the medical device volume down.

4. The method of claim 1, wherein the plurality of functions also includes turning the medical device on, turning the medical device off, turning a medical device volume up, and turning the medical device volume down.

5. The method of claim 1, wherein the operating modes include one or more of a direct audio mode, an omnidirectional microphone mode, or a directional microphone mode.

6. The method of claim 1, wherein a first gesture controls a first function of the medical device and a second gesture controls a second function of the medical device.

7. The method of claim 1, wherein the one or more tags include at least one magnet and the data interface includes one or more sensors configured to detect magnetic fields.

8. The method of claim 1, wherein the one or more gestures comprise a predetermined movement of the one or more tags.

9. The method of claim 1, wherein at least one of the one or more gestures consists only of two of the tags being within about 4 centimeters or less of the data interface.

10. The method of claim 1, further comprising associating the tags with the medical device during a fitting session of the medical device.

11. The method of claim 1, wherein the plurality of tags includes passive RFID tags associated with a recipient of the medical device, wherein the data interface includes one or more antennas for receiving the wirelessly induced signals.

12. The method of claim 1, wherein individual tags correspond to different functions of the plurality of functions.

13. The method of claim 1, wherein the medical device comprises a hearing prosthesis.

14. A medical device, comprising:
a data interface configured to receive wireless signals induced by one or more of a plurality of tags, wherein the wireless signals induced by one or more of the plurality of tags consist of wireless signals induced only by each of the one or more of the plurality of tags passing within about 4 centimeters or less of the data interface, wherein the plurality of tags is associated with a recipient of the medical device; and
a processor configured to interpret the induced signals to identify uniquely each of the one or more of the plurality of tags and to control a plurality of functions of the medical device in response to uniquely identifying the one or more of the plurality of tags, wherein interpreting the induced signals to control a plurality of functions of the medical device comprises selecting, based on the interpretation of the induced signals at the data interface, one of a plurality of operating modes for the medical device, and causing the medical device to operate in the selected operating mode.

15. The medical device of claim 14, wherein interpreting the induced signals to control a plurality of functions of the medical device also includes, based on the interpretation of the induced signals at the data interface, turning the medical device on, turning the medical device off, turning a medical device volume up, and turning the medical device volume down.

16. The medical device of claim 14, wherein the plurality of tags includes at least one passive RFID tag and the data interface includes one or more antennas.

17. The medical device of claim 16, wherein the data interface includes an array of antennas to facilitate the interpretation of gestures made with one or more of the plurality of tags.

18. The medical device of claim 14, wherein the plurality of tags includes at least one passive resonant circuit including one or more of an LC circuit, a ceramic resonator, and a piezoelectric resonator.

19. The medical device of claim 14, wherein the plurality of tags includes a plurality of magnetic field generators for generating unique magnetic fields, and the data interface includes one or more magnetic field readers.

20. The medical device of claim 14, wherein one or more of the plurality of tags is configured to be implanted under the skin of a recipient of the medical device.

21. The medical device of claim 20, wherein one or more of the plurality of tags includes a biocompatible protective layer that allows electrical and magnetic fields to be transmitted therethrough.

22. The medical device of claim 14, wherein one or more of the plurality of tags is coupled to one or more of a glove, ring, bracelet, or watch that can be worn by a recipient of the medical device.

23. The medical device of claim 14, further comprising a microphone configured to receive acoustic signals and an output signal interface configured to transmit output signals to a recipient of the medical device, wherein the processor is further configured to encode the acoustic signals to produce the output signals for transmission to the recipient.

24. The medical device of claim 14, wherein the processor is configured to interpret the induced signals as one or more gestures made with one or more of the plurality of tags.

25. The medical device of claim 14, wherein the plurality of operating modes include one or more of a direct audio mode, an omnidirectional microphone mode, or a directional microphone mode.

26. The medical device of claim 14, wherein the medical device comprises a hearing prosthesis.

27. A method, comprising:
scanning, by a device, for signals induced wirelessly by one or more tags implanted in a user of the device;
processing the wirelessly induced signals to identify one or more gestures made with the one or more tags, wherein each of the one or more gestures consists only of the presence of each of the one or more tags within about 4 centimeters or less of the device; and
performing one of a plurality of functions of the device in response to the one or more identified gestures,
wherein the device is a medical device that is fully implanted in a recipient.

28. The method of claim 27, wherein the recipient and the user are different individuals.

29. The method of claim 27, wherein each of the one or more tags is a self-contained device without a power source directly coupled thereto.

30. The method of claim 27, wherein each of the one or more tags is implanted subcutaneously in one or more fingers of the user.

31. The method of claim 27, wherein the one or more gestures comprise the presence of two of the one or more tags within 4 centimeters of the device.

32. The method of claim 27, wherein the medical device is a hearing prosthesis.

33. A device, comprising:
   a data interface configured to receive wirelessly induced signals from a plurality of tags being held within about 4 centimeters or less of the device; and
   a processor configured to interpret the induced signals as one or more gestures made by one or more of the plurality of tags to control one or more functions of the device, wherein controlling the one or more functions of the device includes increasing a device volume and decreasing the device volume, wherein the one or more gestures consist only of the one or more of the plurality of tags being held within about 4 centimeters or less of the device, and wherein a length of time that the one or more of the plurality of tags is being held within about 4centimeters or less of the device corresponds to at least one of a level of volume increase, a level of volume decrease, a speed of volume increase, or a speed of volume decrease.

34. The device of claim 33, wherein the data interface comprises one or more antennas.

35. The device of claim 33, wherein the data interface comprises one or more magnetic field sensors and the user-coupled means comprises at least one magnet.

36. The device of claim 33, wherein the processor is configured to interpret the induced signals to determine characteristics of movement of the tags.

37. The device of claim 33, wherein the device is a hearing prosthesis.

* * * * *